United States Patent [19]

McCoy et al.

[11] Patent Number: 5,084,263
[45] Date of Patent: Jan. 28, 1992

[54] METHOD OF PREPARING INORGANIC POLYMERIC WATER COMPLEXES AND PRODUCTS SO PRODUCED

[75] Inventors: Charles R. McCoy, Pearland; Frank G. Defalco, Houston, both of Tex.

[73] Assignee: McCoy/Defalco Electrochemics, Inc., Houston, Tex.

[21] Appl. No.: 384,815

[22] Filed: Jul. 24, 1989

[51] Int. Cl.$^5$ .............................. C01B 21/00
[52] U.S. Cl. ..................................... 423/413
[58] Field of Search ......................... 423/413

[56] References Cited

U.S. PATENT DOCUMENTS 4,029,747 6/1977 Merkl ................................. 423/413

Primary Examiner—Wayne A. Langel
Attorney, Agent, or Firm—John R. Kirk; Gordan T. Arnold; Mark A. Oathout

[57] ABSTRACT

The present invention provides aqueous processes which create new chemical compositions of matter prepared by reacting, in the presence of aqueous ammonia or other source of reactive NH$_2$ groups, an alkali metal hydroxide to raise pH above 12, and further reacting with the addition of a mineral acid. The reactants are added as quickly as possible to obtain a highly exothermic reaction which, when reacted in the described manner will then contain ammonia in solution and form new polymeric water complexes. The mineral acid can be selected from, a phosphorus species, or a halogen species, or a nitrogen species, or a sulfur species, or a carbon species, or a combination of these acid species. Chemical complexes formed by these reactions are stable over a wide pH range from 0 to 14+ and can be used to perform many functions in the metal finishing industry; for removing soils from metals; for removing rust from metals; for complexing metal ions; for reducing metallic ores; to act as buffering agents for all acids and alkalis; as broad spectrum germicidal agents; for releasing of organic matter from soils; to act as therapeutic agents for healing of cuts, wounds and burns and abrasions; for healing of topical infections caused by bacteria, viruses, fungi or parasites; as growth stimulators for plants; to precipitate metallic salts from saline solutions; as anti-oxidants for stabilization of free radicals.

14 Claims, No Drawings

METHOD OF PREPARING INORGANIC POLYMERIC WATER COMPLEXES AND PRODUCTS SO PRODUCED

BACKGROUND OF THE INVENTION

The first electroplating patent was granted in 1842 for the deposition of silver through a cyanide medium. Cyanide then became the electrolyte of choice for many electroplating baths for depositing metals of commercial importance such as gold, silver, copper, cadmium and zinc. The stability of the cyanide compound and tolerance of the chemical to upsets have made cyanide the preferred electrolyte in many electroplating operations.

Cyanide is an extremely toxic and hazardous material, and fumes from electroplating baths have to be destroyed, and waste water containing traces of cyanide have to be extensively treated for disposal. With the nation's new found concern for toxic waste, and also the concern for workers in operations where they could be exposed to cyanide fumes, many attempts have been made to find alternative electrolytes to replace cyanide.

Only a few of the alternative plating bath formulations have been able replace cyanide. Silver, gold and copper electroplates still require cyanide for the first strike on a substrate and are a necessary requirement for all electronic electroplating applications.

With the issuance of the first patents on silver electroplating, there were many attempts made to find other nitrogen compounds which could replace cyanide. Many of early experiments were performed using ammonia as a possible candidate for complexing the silver and gold ions for deposition.

It was found that gold or silver in contact with ammonia compounds formed azides and were violently explosive. Since that time, any ammonia containing compound would not be considered for gold and silver electroplating. Other baths formulated for metals which would not explode when in contact with ammonia, such as copper, zinc and cadmium, were developed using electrolytes other than cyanide. However, cyanide remains the electroplaters electrolyte of choice for its stability and efficiency in the plating baths.

Ammonia has been added in minor amounts to many electroplating baths because of its high conductivity and its metal complexing properties. The addition of ammonium hydroxide to the baths are made in such minor amounts that highly exothermic reactions would be avoided. The ammonia fumes, however are less controllable than cyanide fumes and presented strong health hazards in the workplace and in the waste waters. While ammonia is an excellent electrolyte its use in electroplating are severely limited in use to minor additions to some plating baths.

The applicants, in attempting to improve upon the throwing power and conductivity of an electroplating bath, found that ammonia could be absorbed into a zinc plating bath without ammonia fumes coming off during the electroplating process. This was not recognized immediately as a major event by the applicants. However, continued experimentation showed that some new, unusual and surprising phenomena were occurring. This continued experimentation led to the attempts to electroplate silver from the baths. A severe explosion occurred, which led to the temporary abandonment of the silver plating process.

Further experimentation resulted in defining that ammonia could be used provided that the ammonia was reacted in a specific way. It was found, surprisingly, that when ammonia hydroxide was contacted by a alkali metal hydroxide in an aqueous medium and then immediately reacted further by the addition of 85 Phosphoric acid (H3PO4), the ammonia was absorbed in the reaction. The solution was then further reacted to reach an end point 7 Ph or lower and become a clear stable, nitrogen containing solution. Classical chemistry teaches that ammonia cannot remain in solution with an alkali metal hydroxide. Therefore, one of the fundamental rules of chemistry apparently becomes inoperative when the elements are reacted in the manner described in this application.

It was then decided to make a further attempt to electroplate silver from the new compounds developed by the described process. Surprisingly, when silver nitrate, or sliver oxide was placed in the aqueous solution, there are no azide formation, although ammonia was an essential reactant in the formation of the compounds. The silver was then deposited electrolytically on a steel substrate. This was unexpected. Gold was then electroplated using the same techniques for formulation of the electroplating solution.

The applicants then recognized that a fundamental event had occurred in which ammonia could be absorbed in a solution which contained an alkali metal hydroxide. Further, the ammonia would have to be in altered state, otherwise explosions would have occurred. It was further noted that the silver containing solutions prevented silver from becoming photo sensitive, and the silver could be contained in solution an ionic state indefinitely.

During the further experimentation, it became apparent to the applicants that several unusual new properties appeared to be resident in the solution. These included superior buffering qualities, and that any acid—including sulfuric and hydrofluoric acids—and any alkaline could be buffered by the phosphorus based compound. This feature was extremely important when the explosion caused by silver azide formation occurred. McCoy, one of the applicants, was standing viewing the reactor when the explosion occurred and was covered all over his eyes, face and arms with hot boiling alkalis and acids and glass shards.

He was immediately bathed using the phosphoric buffer in his eyes, on his face and arms. The buffer stopped the acid/alkali burns almost instantaneously. An immediate rush visit was made to an eye doctor where glass shards were removed. In two weeks total vision had returned with no residual damage from the acid/alkali burns. Further there was no scarring from the neutralized acid/alkali burns on the face and arms. It was then decided that major therapeutic properties were in the phosphorus compound.

Further reactions were then conducted to determine whether the ammonium hydroxide/alkali metal hydroxide aqueous solution could be absorbed through the chemical reaction with all mineral acids. The acids used were phosphorus species, all halogen species, nitrogen species, sulfur species and carbon species. It was then apparent that ammonia, when reacted in an aqueous solution with other reactants could be changed into a new nitrogen/hydrogen group which provided new chemical compounds through the reaction process. It was further discovered that all the reactants had to be added as rapidly as possible in order to obtain maximum conditions of equilibrium.

Further all of these new compounds had excellent electrolytic properties, could complex metalions, including silver, gold and copper for electroplating, but also exhibited different therapeutic properties when applied to the skin of humans and lower animals. Properties noted were stopping of bleeding from wounds and cuts, disinfections of sores, anti-inflammatory, immediate stopping of pain from cuts and burns, and acceleration of healing without scarring. Further testing showed the compounds to have anti-oxidant properties and could stabilize free radicals. 75% hydrogen peroxide, a powerful oxidant, was stabilized in the phosphorus and sulfur containing solutions and was metastable in the halogen solutions. This indicated the presence of available electrons in the solutions.

Freezing studies were conducted on the compounds. All compounds had changed the freezing point of water. The sodium choride buffer remained water clear to $-23$ F., the phosphorus and sulfur and carbon buffers to $-10$ F. The ice crystals formed by freezing were not the normal tetrahedron ice crystals, and were elongated and slushy. This indicates that a hydrogen bonding mechanism has attached other chemical elements to the water molecule to change the structure of the water. Tests were run with ethylene glycol and methanol and other aldehydes which demonstrates these chemicals were miscible in the new buffers, and could be used as anti-freeze extenders.

A further surprising property was that the new compounds picked up and held an electric charge of up 500 milliamperes and ½ volt. When bimetallic ions of zinc and silver were added the amperage was raised to 750 milliamperes and the charges maintained. Mixtures of the same chemical ingredients which have not undergone the described reactions have much lower charges in solution. This further indicates the presence of active hydrogen and available electrons.

The compounds can complex any metal an ionic state. The compounds can also be formulated of fertilizer components such as phosphorus, nitrogen, potassium, and then a metal ion can be further added by complexing at various parts per million, to act as growth regulators or stimulators, while simultaneously acting as a germicide, if necessary.

The compound's hydrogen ion activity and electron availability showed broad spectrum germicidal capabilities. In addition to disinfection on wounds and burns, these properties help augment the acceleration of healing mechanism in the body. Tests on humans and lower animals showed that any topical infection, whether caused by bacterial, viral, fungal or parasitical strains would respond very quickly to treatment with various types of these new compounds.

It was further found that when aluminum was complexed in the phosphorus solution and the Ph raised above 10, that actinic keratosis or "skin cancer" were instantaneously destroyed, and healing accelerated without scarring. The further application of the same aluminum based compounds showed great efficacy on psoriasis. It is theorized that the high electrode potential of the aluminum ion is responsible for controlling the actinic keratosis.

It is the object of the present invention to provide new nitrogen/hydrogen bearing compounds which allow the combination of elements which could not be combined before is aqueous solutions without salt formation. It is a further object of the present invention to provide a process for the preparation of these new compounds.

As will be readily apparent to those skilled in the art the advantages of these new compounds will be preceived by the following descriptions and the examples.

SUMMARY OF THE INVENTION

The present invention is directed to the production of heretofore unknown chemical compounds formed by highly exothermic reactions, contacting a mineral acid with ammonium hydroxide and an alkali metal hydroxide in an aqueous solution, the resultant complexes so generated by the described reactions, and the aqueous solutions containing same. Classical chemistry teaches that when an alkali metal hydroxide is introduced into an aqueous solution which contains ammonium hydroxide a reaction occurs reducing ammonium hydroxide—(NH 4 OH)—to ammonia gas—(NH 3)—which is then expelled from the solution. That teaching is extant at the present time.

If, however, when the ammonium hydroxide and the alkali metal hydroxide are mixed together, and a strong mineral acid is immediately introduced into the reaction vessel, highly exothermic reactions occur. However, the ammonia is not liberated, but is retained in solution, probably in the form of NH 2, and results in the formation of a new family of inorganic nitrogen containing compounds. It is desirable to add the reactants together as quickly as possible to take advantage of favorable equilibria from the highly exothermic reactions.

Classical chemical theory further suggests that the mixture of a mineral acid, say phosphoric acid, with an alkali hydroxide, say ammonium, the resultant product of reaction would be salt formation such as diammonium phosphate. Classical chemistry also suggests that the addition of one or more concentrated acids into an aqueous medium to react with one or more concentrated alkalis would result in explosive reactions, salt formation, and unstable resulting products. Therefore when ammonium hydroxide is reacted in accordance with the present invention, the ammonia probably as NH2, serves to make new bonds which then prevent salt formation. Surprising, sodium chloride will not form salts when reacted in the described manner.

According to the present invention a quantity of ammonia hydroxide is first introduced into an aqueous medium in an open reaction vessel. Next, an alkali metal hydroxide, preferably potassium hydroxide or sodium hydroxide, is mixed with the ammonium hydroxide by pouring until such time as a stoichiometric condition is reached where no more alkali metal hydroxide can be reacted without salt formation. The reaction is slightly exothermic and at end point, remains a clear aqueous solution. This aqueous solution can then be contacted with amounts of any mineral acid species which could be a phosphorus, or a halogen, or a carbon, or a nitrogen, or a sulfur, or a nitrogen containing acid, or combination of these acids to create a highly exothermic reaction and to continue the reaction until such time as the smell of ammonia gas is no longer present.

This addition of the strong acids to the alkali hydroxide mixture results in highly exothermic reactions with temperatures immediately rising to over 180F. These reactions run from a violent, almost explosive, exothermic reaction when sulfuric is the acid, to less violent exothermic reactions when a phosphorus or carbon acid is reacted, to a controlled reaction when a halogen acid is the reactant. It was found that the use of an open reaction vessel was best suited for the reaction as the violent evolution of heat and gases would give rise to explosive reactions in closed or narrow necked reactor vessels. The reaction does not "run away", but is controllable when reactants are added in the prescribed manner. After initial introduction of the acid into the bases or, vice versa, and the pH starts to change, then the pouring can be accelerated as Ph 12 is approached from the alkaline side or a pH of 2 from the acidic side of the pH scale, the reaction calms down between 4 on the acidic side and 10 on the alkaline side. The reaction can then brought to a desired end point of 7 Ph, and clear stable solutions exist.

It is important that once the feed of acid into the base, or vice versa, is started that the feed be continuous and with slight agitation until the highly exothermic reactions have terminated. The solution should then be brought to a preferred end point of pH 7. Otherwise, salt formation may result in parts of the reaction and some unstable complexes may also form. At this point, new chemical complexes have been formed which remain clear, water soluble, stable solutions which contain an acid species, an alkaline species, and nitrogen/hydrogen groups.

The reaction product first formed in the above example has pH 14+ or a pH of 0+ and can be terminated at that point. However, the reaction should be further pushed to an end point of Ph 7 by the continuous pouring of the reactants together and the reaction terminated.

The resultant clear solutions are stable, water soluble compounds, and have utility as buffers, or as electrolytes, or as germicidal agents.

These new chemical compounds may then be further reacted by the addition of an acid species to lower pH or by the addition of alkali hydroxide to raise pH to any desired end point on the Ph scale. A further surprising and unique property of these buffers is the tolerance to Ph change without salt formation. The complete range of the Ph scale can be run by additions of acids or alkalis to make chemical compounds which are stable from Ph 0 to Ph 14. This stability is critically important in electroplating baths and allows flexibility in electroplating operations and other metal finishing operations; for neutralization of acids and bases; for added germicidal properties; and for stabilization of free radicals.

An indication of the completion of the chemical complex reaction is the absorption of ammonia into the reaction at exothermic peak and the disappearance of the ammonia odor. After reaction, a trace of ammonia is still present in the solution from unreacted ammonia, while the solution is still alkaline. When pH is lowered below 7 all ammonia odor disappears. When the pH is raised above 7 an ammonia odor reappears.

The chemical compounds formed by this invention enable all metals to be complexed in aqueous solutions in all the grouping on the periodic table. Surprisingly, some of the metals complexed chich would previously only be plated through a cyanide medium—such as gold, silver and copper—could be electrodeposited adherently on metallic substrates, using, as electrolytes, compounds from the described reactions. The ability to complex metals and deposit those metals on substrates from aqueous, non-cyanide solutions will greatly lower the levels of toxicity and result in substantial savings for many electroplating processes which require cyanide as a complexing agent.

A further proof of the novelty of these compounds is ability to complex gold and silver in a stable state. Classic chemistry teaches that silver and gold form azides when complexed in ammonia containing solutions, but these metal ions are stable in these new compounds.

It was found through further experimentation that if the ammonium hydroxide/alkali metal hydroxide mixture were maintained at a temperature below 40 F. prior to the addition of the acid complex, then more ammonia would be contained and converted during the exothermic reaction. A further improvement in reaction conditions was noted when deionized water was added to both the alkali components and the acidic components prior to their further reaction.

The use of chilling and addition of water will aid in processing by lowering the level of the exothermic reactions, resulting in a more controlled reaction. Further improvements in processing occur if the alkali metal hydroxide is added to the ammonium hydroxide in the form of flakes or pellets. Continuous slow agitation of the reactants further aids the processing.

A further discovery, occasioned by the addition of water, is that water takes on new properties. The freezing point of water, after undergoing the described chemical reactions, has changed to $-23F$. when using a sodium/chlorine/ammonia compound at a pH of 7. The ice crystals which formed on reaching freezing point were not the normal tetrahedron crystals formed in ice, but were elongated and slushy.

This indicates that a hydrogen bond may be attaching another element to the water molecule and elongating the structure, and thus may account for the changes in the freezing point of the water based solution. Mixtures of the same chemicals which have not undergone the described chemical reactions, freeze at much higher temperatures. Thus it is theorized that water, and its modification from the chemical reactions, are responsible for many of properties available in the new compounds. Electrical characteristics were surprisingly found in the new compounds, which maintained charges up to 500 milliamperes and $\frac{1}{2}$ volt.

To those skilled in the art it will be readily apparent that the described chemical reactions can result in many new, different, stable chemical complexes. Additionally, metal ions can be complexed into the new compounds, and lead to a much larger group of chemicals for purposes of electroplating of metals, and for germicidical purposes and as buffering agents.

The following table lists the species of components which can be combined to form new chemical compounds, by combining one or more elements of each grouping and reacting such elements in the described manner:

| ACID SPECIES | + | REACTIVE NH2 Species | + | ALKALI METAL HYDROXIDES |
|---|---|---|---|---|
| Phosphorus based | | Ammonium Hydroxide | | Sodium Hydroxide |
| Halogen Based Acids | | | | Potassium Hydroxide |
| Chlorine based, | | | | Lithium Hydroxide |
| Fluorine based, | | | | |
| Bromium based, and | | | | |

| ACID SPECIES | + REACTIVE NH2 Species | + ALKALI METAL HYDROXIDES |
|---|---|---|
| Iodine based | | |
| Nitrogen based | | |
| Sulfur based | | |
| Carboxylic Acids such as formic & acetic acids | | |

A formulation would encompass all acids and all alkalines under the following postulates:

(1) One mineral acid plus one alkali metal hydroxide plus ammonium hydroxide (or a source of reactive $NH_2$ groups), (2) Two mineral acids plus one alkali metal hydroxide plus ammonium hydroxide (or a source of reactive $NH_2$ groups), (3) Three mineral acids plus two alkali metal hydroxides plus ammonium hydroxide (or a source of reactive $NH_2$ groups), (4) A multiplicity of mineral acids plus a multiplicity of alkali metal hydroxide, plus ammonium hydroxide (or a source of reactive $NH_2$ groups).

The following are examples of preferred preparation processes.

EXAMPLE

Solution #1

Premix #1

Blend together 200 mL of ammonium hydroxide ($NH_4OH$-26o Baume), 200 mL of deionized water, and 200 mg. 85% KOH pellets or flakes. After mixing the pH is $14^\pm$.

Premix #2

Blend together 200 mL of phosphoric acid and 200 mL of deionized water. After mixing the pH is $0^\pm$ and the temperature is ambient.

Reaction for Neutral pH

Rapidly pour Premix 2 into Premix 1. The initial reaction with temperatures rising to 180F. As premix 2 is added to premix 1, the Ph will start to drop from 14 and around Ph 9, the reaction stops being violent. The rest of premix 2 can be added until Ph 7 is reached. The Ph is now approximately $7^\pm$ and the temperature is approximately 180° F.

The reaction time is less than one minute. A compound containing water, phosphorus, nitrogen/hydrogen groups and potassium are combined in a stable solution. This is the preferred reaction, however ratios of ingredients were varied as follows:

| | AMOUNT OF INGREDIENT | | | | |
|---|---|---|---|---|---|
| INGREDIENT | Run 1 | Run 2 | Run 3 | Run 4 | Run 5 |
| Deionized H2O | 400 ml | 400 ml | 400 ml | 400 ml | none |
| NH4OH | 200 ml | 100 ml | 300 ml | 150 ml | 200 ml |
| KOH | 200 mg | 300 mg | 100 mg | 250 mg | 100 mg |
| H3PO4 | 200 ml | 200 ml | 200 ml | 200 ml | 150 ml |

All reactions result in Ph 7, plus or minus.

EXAMPLE

Solution #2

Premix #1

Blend together 200 mL of ammonium hydroxide ($NH_4OH$—26o Baume), 200 mL of water (D. I.), and 200 mg. of NAOH. After mixing the pH is $14^\pm$.

Premix #2

Blend together 200 mL of phosphoric acid and 200 mL of deionized water. After mixing the pH is $0^\pm$, and the temperature is ambient.

Reaction for Neutral pH

Rapidly pour Premix 2 into Premix 1. The initial reactions is highly exothermic and volatile. After the reaction the pH is $7^\pm$ and the temperature is approximately 180° F. Reaction time is less than one minute. A compound containing water, phosphorus, nitrogen/hydrogen groups, and sodium are combined in a stable solution. This is preferred reaction using sodium hydroxide as reactant, however ratio of ingredients can be varied as shown in the following examples:

| | AMOUNT OF INGREDIENT | | | | |
|---|---|---|---|---|---|
| INGREDIENT | Run 1 | Run 2 | Run 3 | Run 4 | Run 5 |
| Deionized H2O | 400 ml | 400 ml | 400 ml | 400 ml | none |
| NH4Oh | 200 ml | 100 ml | 300 ml | 150 ml | 200 ml |
| NAOH | 200 mg | 300 mg | 100 mg | 250 mg | 100 mg |
| H3PO4 | 200 ml | 200 ml | 200 ml | 200 ml | 150 ml |

All reactions result in Ph 7, plus or minus.

EXAMPLE

Solution #3

Premix #1

Blend together 200 mL of ammonium hydroxide ($NH_4OH$—26o Baume), 200 mL of water (D.I.), and 200 ml of lithium hydroxide. After mixing the pH is $14^\pm$.

Premix #2

Blend together 200 mL of phosphoric acid and 200 mL of water (D.I.). After mixing the pH is $0^\pm$ and the temperature is ambient.

Reaction for Neutral pH

Rapidly pour Premix 2 into Premix 1 stirring continuously. After the reaction the pH is $7^\pm$ and the temperature is approximately 180° F. A stable compound containing water, phosphorus, hydrogen/nitrogen groups, and lithium have been combined in a stable solution.

| | AMOUNT OF INGREDIENT | | | |
|---|---|---|---|---|
| INGREDIENT | Run 1 | Run 2 | Run 3 | Run 4 |
| Deionized H2O | 100 ml | 100 ml | 100 ml | none |
| NH4Oh | 50 ml | 25 ml | 75 ml | 150 ml |
| LiOH | 50 ml | 75 ml | 25 ml | 100 ml |
| H3PO4 | 50 ml | 50 ml | 50 ml | 125 ml |

All reaction result in Ph 7, plus or minus.

EXAMPLE

Solution #4

Premix #1

Blend together 200 mL of ammonium hydroxide ($NH_4OH$—26o Baume), 200 mL of water (D.I.), and 200 mg. of 85% KOH flakes or pellets. After mixing the pH is $14^{35}$.

Premix #2

Blend together 150 mL of 93% H2SO4 and 200 mL of water (D.I.). After mixing the pH is 0±, and the temperature has risen. The temperature is pushed back to ambient by cooling.

Reaction for Neutral pH

Rapidly pour Premix 2 into Premix 1. This initial reaction is violently eruptive. Care should be taken. When the reaction reaches a pH 9± the reaction smooths down. At pH 7 the reaction is terminated and the temperature is 200° F. A compound containing water, sulfur, nitrogen/hydrogen groups, and potassium have been combined in a stable solution. This is the preferred reaction, however ratios of ingredients may be varied as follows:

| Ingredient | Amount of ingredient | | | |
| --- | --- | --- | --- | --- |
| | Run 1 | Run 2 | Run 3 | Run 4 |
| Deionized Water | 400 ml | 400 ml | 400 ml | 400 ml |
| NH4OH | 200 ml | 100 ml | 250 ml | 300 ml |
| KOH | 200 mg | 200 mg | 125 mg | 100 mg |
| H2SO4 | 150 ml | 120 ml | 150 ml | 200 ml |

Reactions result in neutral pH plus or minus. Compounds contain sulfur nitrogen/hydrogen groups, and potassium in clear, stable, water soluble solutions.

EXAMPLE

Solution #5

Premix #1

Blend together 200 mL of ammonium hydroxide (NH4OH—26o Baume), 200 mL of water (D.I.), and 200 95% NAOH pellets or flakes. After mixing the pH is 14±.

Premix #2

Blend together 200 mL of 93% H2SO4 and 200 mL of water (D.I.). After mixing the pH is 0±, and the temperature has risen. Temperature is pushed back to ambient by chilling.

Reaction for Neutral pH

Rapidly pour Premix 2 into Premix 1. The initial reaction is violently eruptive and care should be taken. After the reaction has reached pH 9 the violence subsides and the all of pre mix 2 can be poured into pre mix 1 and terminated at pH of 7±. The temperature is 200° F. A chemical compound containing water, sulfur, nitrogen/hydrogen groups, and sodium have been combined in a stable solution.

The solution is slightly turbid, with suspended particles which precipitate to the bottom of the reaction vessel. The ratios of ingredients can be varied, however this example is the preferred quantities for reaction.

EXAMPLE

Solution #6

Premix #1

Blend together 200 mL of ammonium hydroxide (NH4OH—26o Baume), 200 mL of water (D.I.), and 200 mg. of 85% KOH flakes or pellets. After mixing the pH is 14±.

Premix #2

Blend together 600 mL of hydrochloric acid and 200 mL of water (D.I.). After the mixing the pH is 0±, and the temperature is ambient.

Reaction for Neutral pH

Rapidly pour Premix 2 into Premix 1 stirring continuously. After the reaction the pH is 7± and the temperature is approximately 180° F. A compound containing water, chlorine, nitrogen/hydrogen, and potassium are combined in a stable solution.

| Ingredient | Amount of ingredient | | | | |
| --- | --- | --- | --- | --- | --- |
| | Run 1 | Run 2 | Run 3 | Run 4 | Run 5 |
| Deionized Water | 200 ml | 200 ml | 200 ml | 200 ml | none |
| NH4OH | 200 ml | 100 ml | 300 ml | 100 ml | 200 ml |
| KOH | 200 mg | 200 mg | 150 mg | 100 mg | 200 mg |
| HCl | 600 ml | 450 ml | 700 ml | 300 ml | 600 ml |

Reactions result in neutral pH plus or minus, and is a stable solution containing chlorine, nitrogen/hydrogen groups, and potassium.

EXAMPLE

Solution #7

Premix #1

Blend together 200 mL of ammonium hydroxide (NH4OH—26o Baume), 200 mL of water (D.I.), and 200 95% NAOH pellets or flakes. After mixing the pH is 14±.

Premix #2

Blend together 600 mL of hydrochloric acid and 100 mL of water (D.I.). After mixing the pH is 0±, and the temperature is ambient.

Reaction for Neutral pH

Rapidly pour Premix 2 into Premix 1. After the reaction the pH is 7± and the temperature is approximately 180° F. A compound containing water, chlorine, nitrogen/hydrogen groups, and sodium are combined in a stable solution.

| Ingredient | Amount of ingredient | | | | |
| --- | --- | --- | --- | --- | --- |
| | Run 1 | Run 2 | Run 3 | Run 4 | Run 5 |
| Deionized Water | 200 ml | 200 ml | 200 ml | 200 ml | none |
| NH4OH | 200 ml | 100 ml | 300 ml | 100 ml | 200 ml |
| NAOH | 200 mg | 200 mg | 150 mg | 100 mg | 200 mg |
| HCl | 600 ml | 500 ml | 700 ml | 300 ml | 600 ml |

Reactions produce stable solutions, which are not normal sodium chloride salts, and can be used as a germicidal, as a complexing agent for metal ions.

EXAMPLE

Solution #8

Premix #1

Blend together 200 mL of ammonium hydroxide (NH4OH—26o Baume), 200 mL of water (D.I.), and 200 mg of sodium chloride in 20% saline solution. After mixing the pH is 14±.

Premix #2

Blend together 200 mL of phosphoric acid and 200 mL of water (D.I.). After mixing the pH is 0±, and the temperature is ambient.

Reaction for Neutral pH

Rapidly pour Premix 2 into Premix 1 stirring continuously. After the reaction the pH is 7± and the temperature is approximately 180° F.

A compound containing water, phosphorus, nitrogen/hydrogen groups, and sodium chlorides groups are combined in a stable solution.

EXAMPLE

Solution #9

Premix #1

Blend together 200 mL of ammonium hydroxide (NH4OH—26o Baume), 200 mL of water (D.I.), and 200 mg. of 85% KOH flakes or pellets. After mixing the pH is 14±.

Premix #2

Blend together 200 mL of hydrofluoric acid (HF 52%) and 200 mL of water (D.I.). After mixing the pH is 0±, and the temperature is ambient.

Reaction for Neutral pH

Rapidly pour Premix 2 into Premix 1 stirring continuously. After the reaction the pH is 7± and the temperature is approximately 180° F.

A compound containing water, fluorine, nitrogen/hydrogen groups and potassium are combined in stable solution.

EXAMPLE

Solution #10

Premix #1

Blend together 200 mL of ammonium hydroxide (NH4OH—26o Baume), 200 mL of water (D.I.), and 200 95% NAOH pellets or flakes. After mixing the pH is 14±.

Premix #2

Blend together 250 mL of hydrofluoric acid and 200 mL of water (D.I.). After mixing the pH is 0±, and the temperature is ambient.

Reaction for Neutral pH

Rapidly pour Premix 2 into Premix 1 stirring continuously. After the reaction the pH is 7± and the temperature is approximately 180° F.

A compound containing water, fluorine, nitrogen/hydrogen groups, and sodium are combined in a stable solution.

EXAMPLE

Solution #11

Premix #1

Blend together 200 mL of ammonium hydroxide (NH4OH—26o Baume), 200 mL of water (D.I.), and 200 mg. of 85% KOH flakes or pellets. After mixing the pH is 14±.

Premix #2

Blend together 200 mL of hydrobromic acid and 200 mL of water (D.I.). After mixing the pH is 0±, and the temperature is ambient.

Reaction for Neutral pH

Rapidly pour Premix 2 into Premix 1. After the reaction the pH is 7± and the temperature is approximately 180° F.

A compound containing water, bromium, nitrogen/hydrogen groups, and potassium and combined in a stable solution.

EXAMPLE

Solution #12

Premix #1

Blend together 200 mL of ammonium hydroxide (NH4OH—26o Baume), 200 mL of water (D.I.), and 200 95% NAOH pellets or flakes. After mixing the pH is 14±.

Premix #2

Blend together 200 mL of nitric acid (HNo3—90%) and 100 mL of water (D.I.). After mixing the pH is 0±, and the temperature is ambient.

Reaction for Neutral pH

Rapidly pour Premix 2 into Premix 1 stirring continuously. After the reaction the pH is 7± and the temperature is approximately 180° F.

A compound containing water nitrogen, nitrogen/hydrogen groups, and sodium are combined in a stable solution.

EXAMPLE

Solution #13

Premix #1

Blend together 500 mL of ammonium hydroxide (NH4OH—26o Baume), 500 mL of water (D.I.), and 250 mg. of 85% KOH flakes or pellets. After mixing the pH is 14±.

Premix #2

Blend together 250 mL of nitric acid and 250 mL of water (D.I.). After the mixing the pH is 0±, and the temperature is ambient.

Reaction for Neutral pH

Rapidly pour Premix 2 into Premix 1 stirring continuously. After the reaction the pH is 7± and the temperature is approximately 180° F.

A compound containing water, nitrogen, nitrogen/hydrogen groups, and potassium are combined in a stable solution.

EXAMPLE

Solution #14

Premix #1

Blend together 50 mL of ammonium hydroxide (NH4OH—26o Baume), 100 mL of water (D.I.), and 50 ml of potassium hydroxide. After mixing the pH is 14±.

Premix #2

Blend together 50 mL of hydriodic acid and 100 mL of water (D.I.). After mixing the pH is 0±, and the temperature is ambient.

Reaction for Neutral pH

Rapidly pour Premix 2 into Premix 1 stirring continuously. After the reaction the pH is 7± and the temperature is approximately 180° F.

A compound containing water, iodine, nitrogen/hydrogen groups, and potassium are combined in a stable solution.

EXAMPLE

Solution #15

Premix #1

Blend together 200 mL of ammonium hydroxide (NH4OH—26o Baume), 200 mL of water (D.I.), and 200 mg. of 85% KOH flakes or pellets. After mixing the pH is 14±.

Premix #2

Blend together 200 mL of glacial acetic acid (and 200 mL of water (D.I.). After mixing the pH is 0±, and the temperature is ambient.

Reaction for Neutral pH

Rapidly pour Premix 2 into Premix 1. After the reaction the pH is 7± and the temperature is approximately 180° F.

A compound containing water, carbon, nitrogen/hydrogen groups, and potassium are combined in a stable solution.

EXAMPLE

Solution #16

Premix #1

Blend together 200 mL of ammonium hydroxide (NH4OH—26o Baume), 200 mL of water (D.I.), and 200 95% NAOH pellets or flakes. After mixing the pH is 14±.

Premix #2

Blend together 200 mL of glacial acetic acid (CH3OOH—99%) and 200 mL of water (D.I.). After mixing the pH is 0±, and the temperature is ambient.

Reaction for Neutral pH

Rapidly pour Premix 2 into Premix 1 stirring continuously. After the reaction the pH is 7± and the temperature is approximately 180° F.

A compound containing water, carbon, nitrogen/hydrogen groups, and sodium are combined in a stable solution.

EXAMPLE

Solution 17

200 mL of phosphoric acid and 200 mL of $H_2O$ placed in an open reactor. Solution 2 is prepared by mixing 400 mL of $NH_4OH$ with 400 mL of $H_2O$. Ammonia is then poured into phosphoric acid as rapidly as possible. After initial violent exothermic reaction is stabilized, potassium hydroxide is added until pH 7 is reached. By changing the order or blending reactants a compound containing water, phosphorus, nitrogen/hydrogen groups, and potassium are combined in a stable solution. The order of blending the reactants may vary, however the reactions should be carried out as quickly as possible to avoid ammonia loss.

EXAMPLE

Solution 18

Premix 1

Blend together 400 mL of ammonium hydroxide (NH4OH—26o Baume), 400 ml of water, and 200 ml. of potassium hydroxide. After mixing ph is 14.

Premix 2

Blend together 600 ml of phosphoric acid and 600 ml. of water. After blending pH is 0 and temperature is ambient.

Reaction for Neutral pH

Rapidly pour premix 2 into premix. After reaction, pH is approximately 7 and temperature is 180F. A compound containing water, phosphorus, nitrogen/hydrogen groups, and potassium are combined in a stable solution.

By increasing the amount of ammonium hydroxide in relation to the amount of potassium and/or other metal hydroxide, and increasing the quantity of mineral acid reactant, more ammonium can be absorbed in the solutions. This allows flexibility in formulations by changing the ratios of acids and alkaline.

EXAMPLE

Solution 19

Premix 1

Blend together 400 ml of ammonium hydroxide and 400 ml. of water and 200 ml of potassium hydroxide.

Premix 2

Blend together 400 ml of water, 100 ml of 93% H2SO4, 100 ml of 36% HCl—22o Baume, and 100 ml of phosphoric acid. pH is 0 and temperature is ambient.

Reaction for Neutral pH

Rapidly pour together premix 2 into premix 1. The reaction is highly exothermic. After the reaction the pH is 7 and temperature is 180+F. A compound containing water, phosphorus, sulfur, chlorine, nitrogen/hydrogen groups, and potassium are combined in a stable solution.

EXAMPLE

Solution 20

Premix 1

Blend together 200 ml of water with 200 ml of ammonium hydroxide and 200 ml of potassium hydroxide.

Premix 2

Blend together 200 ml of water, 100 ml of acetic acid and 100 ml of hydrofluoric acid and 100 ml of 36% HCl—22o Baume.

Reaction for Neutral pH

Rapidly pour pre mix two into pre mix one. Reaction is highly exothermic with temperature 180F. plus. A stable solution containing carbon, chlorine, fluorine, nitrogen/hydrogen groups, and potassium was formed.

Experiments 19 and 20 were run to demonstrate that more than one acid can be incorporated into the reaction process by varying the stoichiometric ratios of the reactants to form new compounds.

Unique and very valuable properties of this new family of compounds, is that when the reaction is pushed to, and terminated at, pH 7, the compounds can then be adjusted to any end point of the pH scale and still remain a stable compound without salt formation. In example 1 above, the neutral phosphorus buffer can be adjusted to a pH of 0 by the addition of any mineral acid. The pH can then be raised from that end point to any higher pH value by the addition of the ammonium hydroxide (NH4OH—26o Baume) hydroxide or an alkali metal hydroxide. Thus if a formulation which requires a larger quantity of any element is required, simple addition of an acid or a base will achieve any desired end result.

Electroplating solutions were prepared using 250 mL (125 mL electrolyte plus 125 mL D.I. water) each of solutions from examples 1 through 19. All tests were conducted in 267 mL Hull cell using standard hull cell panels and standard hull cell anodes. A D.C. rectifier with a capacity of 25 volts and 10 amperes was used as the current source.

The metals which were complexed and electroplated, the amperages used, time for deposition, and the type of anode and cathode are described in the Example 1: 250 ml. solution 1 used. pH adjusted from 7 to 4 by adding phosphoric acid. Steel panel inserted as cathode and zinc used as an anode, current applied at 3 amperes for 5 minutes. Coverage of 95% of panel, with 1/10 of a mil thickness. EDAX indicated presence of zinc and phosphorus in deposit.

Substituted stainless steel as cathode and applied current at 3 amperes for 5 minutes. EDAX indicated presence of zinc and phosphorus in deposit. Stainless steel is a passive material and therefore is very difficult to deposit an electroplate adherently on its surface.

ELECTROPLATING EXAMPLES

Example 1

200 ml of solution 1 was placed in a Hull Cell plating bath. Ph of 7 was adjusted to Ph of 4 by addition of phosphoric acid. Steel panel was inserted as cathode and zinc metal electrode 2"×2"×¼" used as anode. Applied current of 3 amps for 5 minutes. Coverage was approximately 98% of panel of 1/10th of a mil thickness. EDAX analysis indicated presence of zinc and phosphorus and deposit.

Example 2

Solution 1 adjusted from pH 7 to pH 4 with phosphoric acid. Panel inserted as cathode and cadmium used as anode. Applied 3 amperes for 5 minutes. Coverage approximately 95% on face of panel of 1/10 mil thickness. EDAX analysis indicated presence of cadmium and phosphorous in the deposit.

Example 3

Solution 1 pH 7 used nickel anode, plated at 3 amperes for 10 minutes indicated deposit of nickel on steel panel.

Example 4

Solution 1 pH 7 used lead anode plated 1 ampere for 15 minutes. Analysis indicated pressure of lead in deposit.

Example 5

Solution 1—pH adjusted from 7 to 11 via addition of ammonium hydroxide and raised to pH 12 by addition of potassium hydroxide. Used zinc anode, plated at 0.2 amperes for 5 minutes. Zinc deposited over 100% on front of panel+ and 15% on back side. Analysis indicated zinc deposit.

Example 6

Solution 1 pH adjusted to 12 as in Example 5. Used cadmium anode and plated 1 ampere for 5 minutes. Deposited cadmium on 100% of the front of the panel. Analysis indicated cadmium deposit.

Example 7

Solution 1 pH of 7 used Canadian Maple Leaf gold coin as anode. Plated at 0.5 amperes for 10 minutes and deposited gold on cathode.

Example 8

Solution 1 adjusted pH to 4 via addition of phosphoric acid. Used molybdenum anode and plated at 1 ampere for 10 minutes. Deposited on 100% of face of cathode. Aluminum plate substituted as cathode and molybdenum deposited at 1 ampere for 10 minutes. Magnesium substituted for aluminum at cathode and molybdenum deposited at 1 ampere for 10 minutes. EDAX analysis indicated presence of molybdenum in deposits on steel, aluminum, and magnesium.

Example 9

Solution 1 pH raised to 11 by addition of $NH_3$ and then to 14 by addition of KOH. Steel panel inserted and tungsten metal anodes used. Current applied at 3 amperes for 1 minutes. Analysis indicated presence of tungsten deposit on steel.

Example 10L

Solution 2 pH lowered to 4 as in Example 1 and zinc anode used. Current applied at 3 amperes for 5 minutes and zinc deposited on 85% of face of the cathode.

Example 11

Solution 2 pH raised to 11 with addition of $NH_3$ and raised to 12 with addition of NaOH. Used cadmium anode with steel cathode. Plated at 0.5 ampere for 5 minutes. Full coverage of deposit on panel.

Example 12

Solution 3 pH 7 used nickel anode and steel cathode 1 ampere for 10 minutes. Nickel deposited on cathode.

Example 13

Solution 4. Raised pH to 8 by addition of ammonium hydroxide. Used nickel anode and steel cathode. Plated at 1 ampere for 10 minutes and nickel deposited on cathode.

Example 14

Solution 4 pH 7. Used copper anode and steel cathode and applied current at 1 ampere for 10 minutes. Copper deposited on cathode.

Example 15

Solution 5 raised pH to 11 with addition of $NH_3$. Used zinc anode and plated at 1 ampere for 5 minutes. Zinc deposited on cathode.

Example 16

Solution 5. Lowered pH to 3.5 with addition of $H_2SO_4$. Used zinc anode and steel cathode plated at 1 ampere for 15 minutes. Zinc deposited on cathode.

Example 17

Solution 6. Lowered pH to 3.5 with addition of HCl. Used zinc anode and steel cathode. Plated at 1 ampere for 10 minutes. Shiny zinc coat deposited on cathode.

Example 18

Solution 6. Raised pH to 11 with $NH_3$. Used cadmium anode and steel cathode. Plated at 2 amperes for 10 minutes, and cadmium deposited on cathode.

Example 19

Solution 6. pH 7. Used molybdenum anode and steel cathode. Plated at 1 ampere for 10 minutes and molybdenum deposited on cathode.

Example 20

Solution 7. Raised pH to 12 with NaOH. Used zinc oxide and steel cathode. Plated at 1 ampere for 5 minutes. Zinc deposited on cathode.

Example 21

Solution 8. Raised pH to 11 with $NH_3$. Used zinc anode and steel cathode. Plated at 0.5 ampere for 5 minutes. Thin shiny zinc deposited over 100% of panel face was deposited.

Example 22

Solution 8. Raised pH to 11 with $NH_3$. Used copper anode and steel cathode plated at 1 ampere for 10 minutes. Copper deposited on cathode.

Example 23

Solution 8. Lowered pH to 4 with $H_2PO_4$. Used zinc anode and steel cathode at 2 amperes for 10 minutes. Bright zinc deposited on cathode.

Example 24

Solution 9. pH 7. Used copper anode and steel cathode. Plated at 1 ampere for 10 minutes. Copper deposited on cathode.

Example 25

Solution 9. Lowered pH to 4 with HF. Used cadmium anode and steel cathode. Plated at 3 amperes for 5 minutes. Cadmium deposited on cathode.

Example 26

Solution 10. Raised pH to 10 with addition of NaOH. Used cadmium anode and steel cathode. Plated at 1 ampere for 5 minutes. Cadmium deposited on cathode.

Example 27

Solution 11. pH 7. Used gold anode and steel cathode. Plated at 1 ampere for 10 minutes. Gold deposited on cathode.

Example 28

Solution 11. Raised pH to 11 with $NH_3$. Used silver anode and steel cathode. Plated at 1 ampere for 5 minutes. Silver deposited on cathode.

Example 29

Solution 12. Lowered pH to 4 with $HNO_3$. Used zinc anode and aluminum cathode. Plated at 1 ampere for 10 minutes. Deposited zinc on aluminum cathode.

Example 30

Solution 13. Raised pH to 10 with $NH_3$. Used zinc anode and magnesium cathode. Plated at 1 ampere for 5 minutes. Zinc deposited on magnesium.

Example 31

Solution 14. pH 7. Used gold anode and steel cathode. Plated at 1 ampere for 12 minutes. Gold deposited on cathode.

Example 32

Solution 15. Raised pH to 11 with addition of $NH_3$. Used copper anode and steel cathode. Plated at 1 ampere for 10 minutes. Copper deposited on cathode.

Example 33

Solution 16. Raised pH to 11 with NaOH. Used zinc anode and steel cathode. Plated at 0.5 ampere for 10 minutes. Deposited zinc on cathode.

Example 34

125 mL of solution 17 added to 125 mL $H_2O$ and placed in hull cell. pH lowered to 3.5 with phosphoric acid. Steel panel used as cathode and zinc used as anode. Applied current at 3 amperes for 5 minutes and zinc deposited on cathode.

Example 35

125 mL of solution 18 and 125 mL of $H_2O$ placed in hull cell. pH adjusted to 12 via addition of NaOH. Used steel panel as cathode and used zinc as anode. Current set at 1 ampere for 5 minutes and zinc deposited on cathode.

Example 36

125 mL of solution 19 and 125 mL of $H_2O$ added to hull cell. pH adjusted to 3 via addition of phosphoric acid. Steel panel used as cathode and nickel used as anode. Current applied at 3 amperes for 10 minutes. Nickel deposited on cathode.

REACTIONS FOR COMPLEXING OF METALS

The first electroplating patent was granted in 1842 for plating of silver through a cyanide medium. There has been little or no change in silver electroplating since that first patent. As the years went on, and as science began to develop the reasons for electrodeposits, the reasons for cyanide's complexing of metals became understood. As a result, the electroplating of gold, copper, zinc and cadmium using the complexing ability of cyanide were developed into very important commercial uses. However, as awareness of cyanide as a health hazard became a problem in the work place, alternative methods of electroplating were sought. Research has been conducted in several attempts to replace cyanide in electroplating baths, with only the alkaline and acidic zinc plating baths being commercially accepted. Even these successes have not been universally accepted by electroplaters as cyanide zinc baths are made easier to control and are more forgiving of impurities. Electroplaters still prefer cyanide zinc electroplating, but legal and moral considerations have forced them to use the non-toxic zinc plating baths currently in use.

The cadmium non-cyanide baths which are being used in a very small percentage of commercial cadmium baths, have many problems and so have gained only minimal acceptance.

Silver and copper cannot be deposited on any substrate for major industrial use applications without a cyanide strike. Cyanide is essential to provide a high quality substrate for noble metals and is also desirable as a substrate for less noble metals such as cadmium, zinc, nickel and other metals.

Surprisingly, the resultant products of chemical reactions described elsewhere in this application exhibit the same complexing ability as cyanide. Therefore, it is now possible to choose, by using one of the many teachings of the present invention, a non-toxic electrolyte with complexing characteristics equal to or greater than cyanide. The inventors have defined through the plating of thousands of panels in the various electrolytes that the preferred composition is a complex of phosphorus, ammonia, and potassium, which when reacted has an end pH approaching 7. This compound can then be further adjusted to the required pH by the addition of acids or alkalis or metal salts.

Following below are examples of the utility of various electrolytes for electroplating.

SILVER PLATING

Silver—Example 1

Premix 1 is prepared by blending 200 mL $H_2O$ + 200 mL $NH_4OH$ with 200 mL KOH.

Premix 2 is 200 ml phosphoric acid plus 200 mL $H_2O$. 10 grams of silver nitrate are dissolved in the solution.

Premix 2 is poured into Premix 1 as rapidly as possible. Explosion occurred. Experiment abandoned.

Silver—Example 2

Added 10 mg of silver oxide to mixture. Explosion occurred. Experiment abandoned.

Silver—Example 3

Premix 1 is prepared by blending 200 mL $H_2O$ + 200 $NH_4OH$ with 200 mL of KOH.

Premix 2 is prepared by blending 200 mL $H_2O$ and 200 mL $H_3PO_4$.

Premmix is poured into premix 1 as rapidly as possible. End point is Ph of 7. Material was allowed to cool down for 3 hours to reach ambient temperature. 100 grams of silver nitrate are dissolved in water and added to solution and pH is lowered to approximately 5. Solution is slightly cloudy. 10 mL of phosphoric acid is stirred in and the pH is raised back to pH 7 or above with $NH_4OH$. Solution is now clear.

Extracted 200 mL of above solution and placed in 267 mL hull cell. Inserted steel cathode and used neutral anode. Applied current at 0.025 amperes for eight minutes. Silver plated 100% on face of cathode and further deposited on rear side of panel.

Substituted silver anode for neutral anode and used steel cathode. Applied current at 0.025 amperes for five minutes. Plated 100% on face of cathode. Note, silver anode tended to passivate or blacken.

Used same solution and substituted Ebonex conductive ceramic electrode as cathode. Applied current at 0.025 amperes for five minutes. Silver deposited on ceramic substrate.

Substituted graphite electrode as cathode. Applied current at 0.025 amperes for 15 minutes. Silver deposited on graphitic carbon and throughout matrix of electrode.

Substituted 0.7 inch OD piece of titanium pipe for graphite for the cathode. Applied current as 0.025 amperes for 10 minutes and silver deposited on titanium.

Substituted 3"×2"×⅛" bobl aluminum alloy as cathode. Applied current at 0.025 amperes for five minutes. Silver deposited on aluminum plate.

Substituted 3"×2"×4" piece of 304 stainless steel as cathode, and applied current at 0.025 amperes for 5 minutes. Silver deposited directly on nickel bearing alloy.

Suprising and unique features of this new silver electroplating technique are as follows:

1. Silver can be stabilized in an ammonia based solution without formation of an azide.
2. Cyanide strike is not required.
3. "Hot lead", whereby the power is activated and the cathode charged when going into solution, is not required.
4. Complexed silver is not photosensitive.
5. Silver can be electroplated on any conductive substrate including materials such as aluminum, titanium, carbon, ceramics, and other substrates upon which silver could not heretofore be plated.
6. Stable solution whereby pH can be adjusted to deposit silver from acidic solution, or a neutral solution or an alkaline solution.

ALUMINUM

A complexed aluminum plating solution was prepared by placing 3-99% purity ¼" diameter×10" long aluminum rods in an open reactor. 200 mL of ammonia and 200 mL $H_2O$ were added to the reactor. 200 mL of KOH flakes were slowly and intermittently added to the vessel containing the ammonia and aluminum metal. This addition started an exothermic reaction which was allowed to continue for 45 minutes and then the aluminum rods are extracted and the reaction terminated. The rods are weighed and 100 grams of aluminum had gone into solution.

Premix 2 was prepared by blending 200 mL $H_3PO_4$ with 200 mL of $H_2O$.

Aluminum premix 2 was slowly poured into premix 1. After initial violent eruptive exotherm, the pouring was continued until a pH of 4.5 was reached and the reaction terminated. 125 mL of this solution was blended with 125 mL of $H_2O$ and placed in a hull cell. A steel panel is inserted as a cathode and a neutral anode is used. Current is applied at 3 amperes for 10 minutes and a metal deposit across 60% of the face of the cathode was noted. EDAX analysis showed deposit to contain aluminum and phosphorous.

pH of plating solution was adjusted by pouring more of premix 1 until a pH of 11 was reached. A further reaction occurred during the blending which was slightly exothermic. A steel panel was inserted as a cathode and the unreactive aluminum rods were used as anodes. Current was applied at 1 ampere for 5 minutes. A thin aluminum plate was deposited across 100% of the cathode.

Since it has been theorized that aluminum could not be deposited from aqueous solution, these results were surprising. This deposit demonstrates the ability of the product of this invention to complex metals heretofore believed not plateable from aqueous solution because of their electronegative electrode potential and place in the electromotive series and to plate those metals on steel substrates.

A further surprising result which demonstrates the utility of these inventions was accidentally discovered. One of the applicants, McCoy, had a spot of psoriasis on the knuckle of his right hand for over 20 years. When contact was made with the aluminum electrolyte, the psoriasis reacted with a stinging sensation. In 24 hours a scab has formed and within 5 more days fell off the spot and the psoriasis was cured. McCoy, after a period of time, then decided to try to heal a "skin cancer" or actinic keratosis lesion on his right forehead and placed the aluminum compounds on affected area. The reaction was immediate and after 24 hours a scab had formed and within 5 to 7 days the scab feel off the healed area. These were truly surprising results from the complexing of the aluminum with the electrolyte. Tests were also run using zinc and copper complexed in the same electrolyte but there was no discernable reaction with the skin cancers.

Cadmium

Premix 1 is prepared by dissolving 25 grams of cadmium oxide in 200 mL of $NH_4OH$ and then contacted with 200 mL $H_2O$ and 200 mL of KOH.

Premix 2 is a mixture of 200 mL $H_3PO_4$ and 200 mL $H_2O$.

Premix 2 is added to premix 1 as rapidly as possible and addition is stopped at approximate pH of 11. 125 mL of solution is transferred to hull cell with 125 mL $H_2O$. Steel panel is used as cathode and cadmium as anode. Current is applied at 2 amperes for 5 minutes and cadmium is deposited on 100% of the face of the cathode. pH is lowered at the plating cell by addition of $H_3PO_4$ until pH of 4.5 is reached. A steel anode is inserted and cadmium anode is used. Cadmium deposited across 80% of the panel.

Copper

A copper complexing plating solution was prepared as premix number 1 by dissolving 20 grams of copper metal in 100 mL of nitric acid. Add 150 mL of phosphoric acid to the copper nitrate solution in an open reactor.

Premix number 2 is prepared by contacting 200 mg of KOH with 200 mL and 200 mL of $NH_4OH$.

Premix #1 is then added rapidly to premix #2 while continuously stirring reaction is terminated at pH 7.5.

125 mL of copper complexed solution and 125 mL of $H_2O$ is placed in hull cell. Steel panel is made a cathode and neutral anode is used. Current is applied at 1 ampere for 30 seconds and an adherent copper strike is plated on the cathode. A copper strike is plated on the cathode. A copper anode is substituted for the neutral anode and pH raised is raised to 11 by addition of $NH_4OH$. Current is applied at 1 ampere for 20 minutes and an adherent build-up of 1/10 of a mil thickness is obtained.

An aluminum cathode is substituted for the steel panel and current is applied at 1 ampere for 45 seconds and an adherent copper strike is obtained on the aluminum.

A zinc die casting is substituted for the aluminum as a cathode in a reactangular shaped box structure (1"×2"×3") which has been specially precleaned. Current is applied at 2 amperes for 5 minutes and an adherent full coverage strike is obtained.

A piece of 316 stainless steel (1"×3") is used as a cathode. No special pretreatment is required. Current is applied to 3 amperes for 1 minute and adherent copper strike is obtained.

Gold

Complexed gold plating solution is prepared by dissolving 2 grams of gold in 20 mL of aqua regia composed of 5 mL $HNO_3$ and 15 mL of HCl. Premix 1 is then made up by adding 50 mL $H_3PO_4$ and 50 mL $H_2O$ to the dissolved gold.

Premix 2 is prepared by contacting 50 mL of KOH with 50 mL of $NH_4OH$ and 50 mL of $H_2O$.

Premix 2 is poured rapidly into premix 1 and reaction terminated at pH 7.

125 mL of gold solution is transferred to a hull cell and 125 mL D.I. $H_2O$ is added. A steel panel is inserted as a cathode and a dimensional stable anode is used. Current is applied at 0.5 ampere for 5 minutes and an adherent gold strike on steel is obtained.

pH of solution is raised to 10 by addition of $NH_4OH$. Steel panel is inserted as cathode and current applied at 0.5 ampere for 3 minutes and adherent gold deposit obtained.

pH of solution is lowered to 5 by addition of $H_3PO_4$ and a steel panel inserted as cathode. Current is applied at 1 ampere for 5 minutes and adherent gold deposit is obtained.

Molybdenum

Premix #1 is prepared by dissolving 50 grams of molybdenum metal powder in 100 mL of $HNO_3$ and 200 mL of water. After all molybdenum is dissolved, 300 mL of $H_3PO_4$ and 300 mL of water are added to the moly/nitrate.

Premix #2 is prepared by contacting 300 mL $NH_4OH$ with 300 mL of $H_2O$ and 300 mL of KOH dry flakes. Solution is stirred constantly. pH is 14+.

Premix #1 is now poured into premix 2 as rapidly as possible, stirring constantly, until a pH of 7 is reached. Immediate reaction of pouring premix 1 into premix 2 is a violent exothermic reaction and a rise in temperature to above 180° F. As more of the premix 1 is dissolved in premix 2, the reaction slows down and ammonia is all absorbed or converted to $NH_2$. pH measurement after 600 mL of premix 1 has been reacted with premix 2 is approximately 11. Temperature of the alkaline solution is too high to use a calibrated pH meter so pH papers are used to estimate pH. Temperature is measured at 190° F.

A hull cell steel panel is cleaned and submerged in the molybdenum solution. After 3 minutes the panel is extracted from the solution and molybdenum has electrolessly deposited over 100% of the panel.

The pH of the solution is lowered further by reacting more of premix 1 until pH 7 is reached.

125 mL of molybdenum solution and 125 mL of $H_2O$ are added to hull cell. A steel panel is inserted in the hull cell as cathode and a neutral anode is used. Current is applied at 1 ampere for 5 minutes and molybdenum is deposited on 100% of the face of the cathode, and 68% of rear of the cathode.

Solution pH is lowered to 5 by the addition of phosphoric acid. A steel panel is inserted and plated at 2 amperes for 5 minutes and molybdenum is deposited on the cathode.

All of the three plating tests were reproduced using aluminum and magnesium as cathodes and molybdenum was again deposited at the same amperage on all six cathodes.

Since molybdenum cannot be electroplated using conventional technology, these results were indeed suprising. An even further unexpected result was the deposition electrolessly of molybdenum on reactive metals such as aluminum and magnesium. These metals are so electronegative that they cannot be electroplated except under very difficult and very precise conditions.

Nickel

A complexed nickel plating solution was prepared as premix 1 by dissolving 50 grams of nickel metal powder in 200 mL of $HNO_3$ plus 200 mL of $H_2O$. A blend of 200 mL $H_3PO_4$ and 200 mL of water was added to the nickel nitrate.

Premix 2 was prepared by contacting 200 mL of $NH_4OH$ with 200 mL $H_2O$ and 200 mL KOH.

Premix 2 was poured into premix 1 and reaction terminal at pH 4. 125 mL of nickel complex solution plus 125 mL $H_2O$ were blended and placed in a 3"×6"×3" plating cell. An aluminum disc was inserted as cathode and nickel was used as anodes. Current was applied at 2 amperes for 3 minutes and nickel was deposited in the aluminum. A steel hull cell panel was then substituted for the aluminum as a cathode and the current applied at 3 amperes for 5 minutes and nickel was deposited across 100% of the panel face.

Reaction was then continued by pouring the balance of premix 2 into premix 1 until pH 7 was reached. The pH of the solution was then adjusted upwards with $NH_4OH$ at a pH 11, the green nickel solution started changing color to blue. At pH 12 the solution was blue and the reaction terminated. Since the blue color is unknown in nickel electroplating solutions, it was decided to attempt to electroplate nickel in this transition state. 125 mL of solution and 125 mL of H$_2$O were blended together and placed in the above described plating cell. A steel panel was used as cathode and nickel as an anode. Current was applied at 1 ampere for 3 minutes and a bright nickel deposit on steel resulted. The pH of the solution was adjusted via addition of H$_3$PO$_4$ and the color of the solution changed back to green.

Tungsten

Premix 1 is prepared by placing 25 grams of tungsten metal powder into 200 mL of aqua regia. Tungsten goes slowly into solution in 72 hours. 200 mL of water and 200 mL of H$_3$PO$_4$ are added to the dissolved tungsten solution.

Premix 2 is prepared by contacting 200 mL of NH$_4$OH with 200 mL of H$_2$O and 200 mL of KOH.

Premix 1 is added to premix 2 stirring continuously until pH of 7 reached. Temperature is allowed to cool to ambient and then 125 mL of tungsten complex and 125 mL of H$_2$O. Used steel panel as cathode and a neutral anode. Current applied at 3 amperes for 10 minutes. Thin tungsten deposit on surface of panel. Substituted aluminum panel and magnesium panels for steel as cathodes and plated at 1 ampere for 5 minutes. Tungsten deposited on both metals.

The above solution was raised to pH 14 via addition of KOH flakes. A tungsten anode was fashioned by tying together six tungsten 0.25" electrodes used in TIG welding to gain enough surface area to draw current and prevent polarization of the anodes. A steel panel was inserted as cathode and current applied at 3 amperes for 15 minutes. Tungsten was deposited on cathodes and anodes showed uniform erosion indicating tungsten dissolution in aqueous solution and plating out on cathode.

Zinc

Premix 1 is prepared by dissolving 20 grams of zinc oxide in 200 mL of NH$_4$OH, and then contacted with 200 mL of H$_2$O and 200 mL of KOH.

Premix 2 is 200 mL of H$_3$PO$_4$ and 200 mL of H$_2$O.

Premix 2 is added rapidly to premix 1 stirring constantly until a pH between 6 and 8 is reached and the reaction is then terminated.

125 mL of zinc ph 7 solution is added to 125 mL distilled H$_2$O and placed in hull cell. pH is lowered to 3.5 by addition of 25 mL H$_3$PO$_4$. A steel panel is inserted as cathode using zinc anodes. Current is applied at 3 amperes for 5 minutes and is deposited over 95% of face of cathode with preferred current density ranges on hull cell short of approximately 18 to 30 ASF.

125 mL of zinc pH 7 solution is added to hull cell with 125 mL of distilled H$_2$O. Approximately 60 mL of KOH is added to solution and pH raised to 12.5. Steel panel is inserted as cathode and zinc anodes used. Current is applied at 1.5 amperes for 3 minutes. Zinc is deposited over 100% of the face of the panel. At the area of highest current density build-up was such that zinc was burned and passivated. Hull cell tables indicated a preferred current density range of under 5 ASF. Substituted aluminum and magnesium as cathodes and electroplated zinc at 2 amperes for 5 minutes. Zinc metal deposited adherently on both of these reactive metals.

Approximately 10 mL of HCL was added to alkaline zinc and pH lowered to 12. Steel panel used as cathode and current applied 11 amperes for 3 minutes. Plated panels were compared and coverage. Throwing power and preferred current density were substantially the same; however, the addition of the HCL resulted in a brighter zinc deposit.

The properties of this new group of compounds indicate to ability to complex any metal ion in solution from the following groups of elements in the periodic table:

Group IB: Copper, Silver, Gold
Group IIA: Beryllium, Magnesium
Group IIB: Zinc, Cadmium
Group IIIA: Aluminum, Gallium, Indium
Group IVA: Silicon, Tin, Lead
Group IVB: Titanium, Zirconium, Hafnium
Group VA: Antimony, Bismuth
Group VB: Vanadium, Niobium, Tantalum
Group VIA: Selenium, Tellurium
Group VIB: Chromium, Molybdenum, Tungsten
Group VIIB: Manganese
Group VIIIB: Iron, Cobalt, Nickel, Palladium, Rhodium Reduction of oxides and sulfides of the above cited elements to metals can also be accomplished by the use of these new compounds.

Electroplating baths often require that buffering compounds be used to retard build up of acids and alkalis during operation. The superior buffering qualities and electrolytic qualities make these compounds of value for buffering those elements. The ability to absorb any acid or any alkaline chemical and neutralize those compounds, is a very important application in acid and alkaline spills and neutralizing chemical burns.

Further experimentation determined the compounds ability to release metallic salts from saline solutions. Oil field brine from the Smackover formation in Smackover, Ark. was used as the test saline solution.

Example 1

100 ml of saline solution was placed in flask. This was then contacted with 1 ml of solution #1—phosphorus, nitrogen/hydrogen, potassium—and salts slowly started to flocculate and precipitate to bottom of flask. No agitation was required. Water was now potable.

Example 2

100 ml of saline solution was placed in flask. This solution was then contacted with 1 ml of solution #4—sulfur, nitrogen/hydrogen, and potassium—and salts slowly started to flocculate and precipitate to bottom of flask. Water was potable in 30 minutes.

Example 3

100 ml of saline solution was placed in flask. This was then contacted with 1 ml of solution #7—chlorine, nitrogen/hydrogen, and potassium. Salts slowly started to flocculate and precipitate to bottom of flask. Water was potable in 30 minutes.

Example 4

100 ml of saline solution was placed in flask. This solution was then contacted with 1 ml of aluminum plating solution—phosphorus, nitrogen/hydrogen, potassium. Salts started to string out and precipitate to bottom of flask. Water was potable in 10 minutes.

It is theorized that the active hydrogen ion in these compounds changes the charges between the water and the salt in solution, freeing the bonds, which then will allow the salts to precipitate.

Samples were taken of various solutions and place in General Electric deep freeze at minus 10F. Bottles used in the experiments were from Gerber's Baby Foods.

Solution 1—PNH2K—Water clear after 24 hours, no ice formation.

Solution 2—PNH2NA—Water clear after 24 hours, no ice formation.

Solution 4—SNH2K—Slightly turbid, slushy after 24 hours.

Solution 5—SNH2Na—Slightly turbid, slushy after 24 hours.

Solution 6—ClNH2K—Water clear after 24 hours, no ice formation.

Solution 7—ClNH2Na—Water clear after 24 hours, no ice formation.

Solution 10—FlNH2Na—Water clear after 24 hours, no ice formation.

Solution 11—NNH2Na—Water clear after 24 hours, no ice formation.

Solution 16—CNH2Na—Slightly turbid, slushy after 24 hours.

100 ml each of solution 2 and solution 7 were then taken to lower temperatures by suspending in a mixture of dry ice and methanol.

Solution 7 formed icy slush at −23F. It was then mixed with equal parts of ethylene glycol and lowered further in temperature to new slush formation at −40F.

Solution 1 froze at −20F. in the methanol and dry ice bath.

Electrical measurements were taken on electrical phenomena in the solutions. The solutions carried a charge of 500 milliamperes, plus or minus, and ½ volt, whether the amount solution was 1 ml or 1000 ml. This current is stable and does not dissipiate while the solutions are in storage.

100 ml of the aluminum, phosphorus, nitrogen/hydrogen, potassium plating solution was mixed with 100 ml of the zinc, phosphorus, nitrogen/hydrogen, potassium plating solution. Ph of both solutions were 12+. A gel started to form and with the addition of phosphoric acid the solution was reduced to 7 ph, at which point a solid gel was formed. Electric current measurements were taken and were stable at 500 milliamperes and ½ volt.

100 ml of the silver, phosphorus, nitrogen/hydrogen, potassium plating solution was mixed with 100 ml of the zinc, phosphorus, nitrogen/hydrogen, potassium plating solution, and pH lowered to 7 by the addition of phosphoric acid and a solid gel formed. Electrical measurements were taken and the gel was generating 700 milliamperes and more than ½ volt.

The ability to hold the current changes indicated the presence of available electrons in the solutions, and indicates potential for storage batteries.

Based on these test data it was decided to conduct further experimentation to determine if the electron availability would stabilize oxidants or free radicals.

Hydrogen peroxide ($H_2O_2$) of 75% concentration was chosen as the oxidant.

100 ml each of five different solutions were chosen to demonstrate whether free radicals could be scavenged.

Solution 1—PNH2K—20 ml of H202 was added to 100 ml of solution. After 24 hours, the hydrogen peroxide was still stable. A catalyst of cobalt chloride was then added to see if the peroxide would be released. The addition of the CoCl started to the peroxide to slowly release, and continued over a period of one hour.

Solution 4—SNH2K—20 ml of H202 was added to 100 ml of solution. After 24 hours, the hydrogen peroxide was still stable. A catalyst of cobalt chloride was then added, but the peroxide would not release. 20 ml of 30 API gravity crude oil was added to the solution. The peroxide then began to release slowly over approximately one hour.

Solution 7—ClNH2Na—20 ml of H202 was added to 100 ml of solution. The peroxide became meta-stable and started to release very slowly and continued to release for two hours, Solution 11—NNH2Na—20 ml of H202 was added to 100 ml of solution. After 24 hours the peroxide was still stable.

Solution 16—CNH2Na—20 ml of H202 was to 100 ml of solution. The peroxide became meta-stable and started to release very slowly over two hours.

These experiments were run to determine if electrons in solution could stabilize powerful oxidants and thus also stabilize free radicals.

Further experiments were then run with solution 1 containing hydrogen peroxide. A 3/16th by 3" tungsten welding electrode was placed in the solution. The solution slowly dissolved the tungsten metal, and 24 hours later the tungsten was completely in solution. It is theorized that the slow release of the hydrogen peroxide acting synergistically with the solution reduced the tungsten metal. Therefore a new tungsten reduction process has been found.

10 grams of molybdenum metal were then placed in 100 ml of Solution 1 and 20 ml of hydrogen peroxide. The molybdenum went rapidly into solution within one hour. The slow release of the H202 is theorized to be the reducing agent.

Other metals which were dissolved in like solutions were nickel, and chromium, both of which are difficult metals to reduce. Further tests were run on reduction of iron oxides on rusty steel parts. The iron oxides were readily solubilized in the peroxide containing solutions, derusting the substrate.

a major problem in electroplating operations is the removal of oils and soils from metals in order to have adherent deposits. While many technologies exist to accomplish these tasks, the removal of the oil from the metals creates another problem in the rinse water. The released oils generally become emulsified and are not easily separated from the water. One of the more common means of separation of oils is through vacuum distillation, which is costly. A surprising feature of the new compounds is that when they are added to water, there is enough of a charge imparted to the water that the oil water emulsion is broken. The oil then migrates to the top of the tank where it can then be skimmed off at a substantial reduction in cost.

The current concern for our ecology has highlighted the past practices of disposing of chemical toxic wastes. The disposal of fractions of hydrocarbons and other organic matter have generally been handled by dumping into settling ponds and into clay lined pits. These pits and ponds are in numerous locations around the nation, and the Environmental Protection Agency has identified over 6,000 of these locations. Also during the late 19th century gas for street lighting was manufactured from coal. The residues from this processes which were created decades ago, are located in sites that are now urban population areas. These sites have also been labeled as toxic waste sites, which will have to be cleaned up.

Due to the nature of these emulsions, the only current technology for disposing of the wastes is incineration. A major cost reduction in incineration could be obtained if the organic matter could be readily separated from the soils and the organics then concentrated where they could then be incinerated without also having to incinerate the soils. Further, where clays are involved for lining of pits and ponds, the bond of the clay for the oils is such that there are no known techniques for separation. A compound which could be used to release oil from clays and be cost effective would be extremely valuable for cleaning up certain toxic waste sites.

A gallon sample of a tight emulsion of water, sand, oil, and char was received from the Electric Power Research Institute to see if separtion could be made by the new compounds.

100 ml of the phosphorus, nitrogen/hydrogen, potassium was mixed with 6 liters of water. One liter of the emulsion was placed in a separate glass extraction flask with a valve in the bottom. A rubber hose was connected to the valve and connected with the vessel containing the solution. This vessel was then positioned approximately 3 feet higher than the extraction flask; the valve was opened and slow gravity feed of the solution separated the organic matter and water from the soils and floated the organics to the top of the flask where they could be recovered. This experiment was designed to demonstrate that organic matter in a tight emulsion could be separated from the soils and also from water emulsion.

Samples of an emulsion of oil, acid, water, clay and soils were obtained from the Texaco oil disposal pit at that company's Port Arthur refinery. The tests were run to demonstrate that organic matter could be separated from this type of emulsion by chemical means. The Texaco pit is over 60 acres in area and several feet deep.

Three different solutions were chosen to attempt to break the Texaco emulsion. Solution 1, Solution 4 and Solution 6.

10 ml of Solution 1 was mixed with 500 ml of water. The temperature was raised to 110F. and 30 ml of emulsion was placed in with the solution in a reactor flask. Organic matter slowly started to ascend to the top of the vessel and after 24 hours there were four separate layers; on top was an oil phase, then the solution phase, then the heavy organic phase and then the soil phase. Slight agitation was employed.

10 ml of solution 1 was mixed with 500 ml of water and 10 ml of hydrogen peroxide in a reaction flask. 30 ml of emulsion was then added to the reactor flask. The peroxide slowly started to release from solution and helped to separate the organic matter from the soil. Some of the peroxide bubbles were entrapped in the heavy organic matter thereby lightening the matter and allowing it to float. After 24 hours there were 3 distinct phases; the top being oil and heavy organic matter and some peroxide, layer two was the solution and the bottom layer was the soils. The addition of peroxide helped to lighten the heavy organic by becoming entrapped, and also made the sand and clay appear to be cleaner.

10 ml of solution 4 was mixed with 500 ml of water in a reaction flask. 30 ml of oil emulsion was then placed in the reactor flask. Temperature was raised to 110F. and slight agitation was used. After 24 hours most of emulsion had been broken and separated. After 48 hours 4 phases existed in flask with oil layer, chemical layer, heavy organics layer and soil layer.

10 ml of solution 7 was mixed with 500 ml of water in a reaction flask. 30 ml of oil emulsion was then placed in the reactor flask. Temperature was raised to 110F. and slight agitation was used. After 24 some of the emulsion has broken loose. Temperature was then raised to 125F. and more agitation was used. After 48 hours a complete separation had occurred and there were four distinct phases.

The tests were run to demonstrate that the new chemical compounds could break tight oil/water emulsions which have clay in the matrix. It is theorized that these new compounds have a more positive charge which then unites with the OH-groups on the clay, thereby releasing the oil and water.

These new compounds can be highly useful in the cleaning up of toxic waste sites. Not only can the compounds separate oil from water, and also, importantly oil from clay, but will float the organics in such a manner that the costs of incineration will be substantially reduced.

As the applicants became more invovled with developing the electroplating processes, it became more and more apparent that valuable therapeutic properties were present in the compounds. This led the applicants to start using the compounds for various therapeutic purposes on themselves. In addition to the discovery by McCoy that actinic keratosis and psoriasis and the neutralization of the hot boiling acids and alkalis would respond favorably to application of the compounds on the local areas, if was believed that the compounds had to be non-toxic. The use of the compounds for electroplating purposes, resulted in the materials being inadvertently placed all over their skins with no seeming side effects.

Fungal problems from athlete's feet were instantly disposed with the use of the phosphorus, nitrogen/hydrogen, potassium compounds. In addition, herpes I lesions and cancer sores responded favorably to just one or two treatments with the phosphorus based compound. It was further discovered to immediately relieve the pain caused by burns and wound, and if applied soon enough, to heal the burns and wounds without damage to the skin.

Defalco had two problems which responded favorably to the compounds. These problems were diverticulitis, a stomach disorder, and superficial punctate keratitis-Tyge Elson-a rare virus which caused lesions on the cornea. When it was determined that the compounds were non toxic, he then started mixing one teaspoon of the sodium/chloride/nitrogen/hydrogen buffer in a glass of water and drinking after every meal. After 30 days, the amount was reduced to one teaspoon in a glass of water daily. The diverticulitis was controlled by the chlorine, nitrogen/hydrogen, sodium compound with no toxic side effects. Further, acid indigestion could be completely controlled through the use of the sodium chloride based compound.

The corneal problem had been ongoing for three years and was being controlled the use of contact lenses. It was then decided to see if the healing properties available in the compounds would help heal the keratotic lesions on the cornea. A mixture of 1/6th of phosphorus, nitrogen/hydrogen potassium Solution 1, and 1/6th of the chlorine, nitrogen/hydrogen, sodium Solution 6, and the balance was made up with the addition of ⅔ ionized water. The compound was applied one drop twice daily in each eye for 10 weeks and the use of soft contacts were no longer required. The lesions then recurred several times but could always be healed within 5 to 10 days with no toxic side effects. After a period of 19 months of treatment the lesions ceased recurring. This test indicates that many ocular infections caused by bacteria, virus, fungus or parasites can be controlled by use of these non-toxic germicidal compounds.

An ear infection was healed by the same mixture by placing two drops in the left ear. After stinging sensation the pain cause by the infection vanished within a few minutes, pain was ameliorated and hearing was restored.

The same mixture was used to control sinus infections and hay fever by spraying in the nasal passages.

Several different compounds were made up and tested for antibacterial activity levels.

Solution 1

Phosphorus, nitrogen/hydrogen, potassium was complexed with 10 PPM of silver. This compound was active against *Escheria coli*. The compound was also found to be active against Enterobacter, *Brevibacterium acetylicium*, as isolate of Pseudomonas. This compound was also found to be active against parasites.

Solution 1

Phosphorus, nitrogen/hydrogen, potassium was complexed with 10 PPM of silver and 10 PPM of iodine. This compound showed high activity level against bacteria and parasites.

Solution 1

Phosphorus, nitrogen/hydrogen, potassium was complexed with 10 PPM of platinum. This compound was active against bacteria and parasites.

Solution 6

Chlorine, nitrogen/hydrogen, sodium was complexed with 10 PPM silver nitrate. Ph was adjusted to 9 with NAOH. This compound was then tested for bactericidal activity at the following concentration, using water as the diluent:

| BACTERIAL STRAIN | PERCENT OF SOLUTION CONCENTRATION | COLONIES KILLED |
|---|---|---|
| *Escherichia coli* | 1.06 | 100 |
| *Pseudomonas aeruginosa* | 6.25 | 100 |
| *Streptococcus faecium* | 50.00 | 100 |
| *Staphylococcus aureus* | 100.00 | 92 |

These tests were on run on more than 1000 colonies for each bacterial strain. These tests demonstrate that broad spectrum germicidal activity is present in the compounds.

All the chemical components used in the described reactions were from commercially available stock materials. The use of reagent grades of chemicals did not appear to enhance the reaction parameters. While the use of reagent grade materials will be important in the manufacture of pharmaceutical products, all the compounds which were found to be effective as germicides were made up from either CP (commercially pure) or from technical grade materials. This will result in substantial savings in the industrial applications of the germidical compounds.

It is recognized by the applicants that changes in the percentages of the active ingredients in the chemicals used, generally by the mere addition of water; however, this does not change the basic parameters of the reaction. The descriptions of the reactants and the reactions are intended to disclose the technology so that a person skilled in the art can run these reactions with off the shelf chemical compounds. For instance the reaction can be run using ammonia gas, but the use of commercially available NH4OH is easier and safer in developing the proper reaction.

The use of potassium hydroxide pellets and flakes and sodium hydroxide pellets and flakes are preferred over the hydroxide solutions. It is believed that the higher the pH towards 14 on the alkaline side results in a better reaction by causing a higher exothermic reaction. It is also believed that the lower towards 0 pH the acidic solution is, the better the reaction. Therefore concentrated acids are preferred reactants.

The foregoing descriptions have been directed to particular embodiments of the invention in accordance with the requirements of the patent statutes and for purposes of illustration and explanation of manufacture and use. It will be apparent to those skilled in the art that many modifications and changes in the procedures set forth will be possible without departing from the scope and spirit of the invention. It is the applicants intention to embrace all such modifications and variations.

The subject matter the applicants claim as their invention is:

1. A method of producing inorganic polymeric water complexes stable throughout the pH range from 0 to 14 which comprises reacting in an aqueous medium:
    a. at least one acid selected from mineral acids, formic acid and acetic acid;
    b. an alkali metal hydroxide; and
    c. a source of reactive $NH_2$ groups: said stable water complex prepared according to the following sequence:
        i. providing in aqueous medium in a reaction vessel, a source of reactive $NH_2$ groups;
        ii. adding said alkali metal hydroxide to the reaction vessel in the presence of said source of $NH_2$ groups raising pH of the solution above 12 to a value approaching 14 to form an aqueous ammonium hydroxide/alkali metal hydroxide mixture;
        iii. adding, in the vessel, the acid to the alkali mixture of step ii, at a rate sufficient to create a highly exothermic reaction, and to continue adding reactants together as quickly as possible so that the reactive $NH_2$ groups are contained in solution during formation of the inorganic polymeric water complexes.

2. The method of claim 1, wherein said source of $NH_2$ groups is aqueous ammonia.

3. The method of claim 2, wherein said source of aqueous ammonia is provided by bubbling gaseous ammonia through said aqueous medium.

4. The method in claim 1, wherein the reaction is cooled during the mixing of the alkali metal hydroxide and the ammonia hydroxide.

5. The method in claim 1, wherein the alkali metal hydroxide is potassium hydroxide.

6. The method in claim 1, wherein the alkali metal hydroxide is sodium hydroxide.

7. The method in claim 1, wherein the alkali metal hydroxide is lithium hydroxide.

8. The method of claim 1 wherein the acid is a mineral acid.

9. The method in claim 8 wherein the mineral acid is a phosphoric acid.

10. The method in claim 8 wherein the mineral acid is sulfur acid.

11. The method in claim 8 wherein the mineral acid is any halogen species acid.

12. The method in claim 8 wherein the mineral acid is nitric acid.

13. A method of producing inorganic polymeric water complexes stable throughout the pH range from 0 to 14 which comprises reacting in an aqueous medium:
   a. at least one acid selected from mineral acids and carboxylic acids;
   b. an alkali metal hydroxide; and
   c. a source of reactive $NH_2$ groups: said stable water complex prepared according to the following sequence:
      i. providing in aqueous medium in a reaction vessel, a source of reactive $NH_2$ groups;
      ii. adding said alkali metal hydroxide to the reaction vessel in the presence of said source of $NH_2$ groups raising pH of the solution above 12 to a value approaching 14 to form an aqueous ammonium hydroxide/alkali metal hydroxide mixture;
      iii. adding, in the vessel, the acid to the alkali mixture of step ii, at a rate sufficient to create a highly exothermic reaction, and to continue adding reactants together as quickly as possible so that the reactive $NH_2$ groups are contained in solution during formation of the inorganic polymeric water complexes.

14. The method in claim 13 wherein the acid is a carboxylic acid.

* * * * *